United States Patent [19]

Davis et al.

[11] 3,932,695

[45] Jan. 13, 1976

[54] REACTANT SHEET FOR DEVELOPING COLORLESS DYE IMAGES

[75] Inventors: Gerald T. Davis; Robert A. Fetters, both of Chillicothe, Ohio

[73] Assignee: The Mead Corporation, Dayton, Ohio

[22] Filed: Jan. 23, 1967

[21] Appl. No.: 610,766

[52] U.S. Cl. ............... 428/531; 427/145; 427/146; 427/150; 427/152; 427/203; 428/914
[51] Int. Cl.$^2$ .................. B32B 27/08; B32B 27/42; B41M 3/12; B41M 5/00
[58] Field of Search ............... 117/155 L, 1.7, 36.2; 260/51; 427/145, 146, 203, 150, 152; 428/524, 537, 914, 530, 531

[56] References Cited
UNITED STATES PATENTS

| | | | |
|---|---|---|---|
| 1,277,904 | 9/1918 | Gesell | 117/155 |
| 2,463,501 | 3/1949 | Arvin | 260/51 |
| 2,972,547 | 2/1961 | Tien | 117/36.2 X |
| 3,020,170 | 2/1962 | Macaulay | 117/36.2 X |
| 3,244,549 | 4/1966 | Farnham et al. | 117/36.2 |
| 3,244,550 | 4/1966 | Farnham et al. | 117/36.2 |
| 3,296,965 | 1/1967 | Reif et al. | 117/17.5 X |
| 3,322,557 | 5/1967 | Schwab | 117/36.2 |
| 3,374,768 | 3/1968 | Lawes et al. | 117/17.5 X |
| 3,466,184 | 9/1969 | Bowler et al. | 117/36.2 |

*Primary Examiner*—Michael R. Lusignan
*Attorney, Agent, or Firm*—Wilson G. Palmer; Lawrence B. Biebel

[57] ABSTRACT

A relatively uniform thin coating of a solid phenolic reactant can be applied to a paper base by contacting said paper base with a thin film of a solution consisting essentially of said phenolic reactant in a volatile organic solvent and immediately evaporating said solvent and, unexpectedly, said phenolic reactant is retained essentially completely on the contacted surface of the paper base. Thusly applied, it has been found that well defined colored marks are formed on the surface of the paper base on marking the surface with a colorless marking ink.

3 Claims, No Drawings

REACTANT SHEET FOR DEVELOPING COLORLESS DYE IMAGES

FIELD OF THE INVENTION

This invention relates to the production of a reactant sheet for use as a receiving and color developing sheet for colorless dye images and to a method of developing such images.

PRIOR ART

Reactant sheets of this type are usually used in conjunction with a transfer sheet which contains a colorless marking ink such as crystal violet lactone dissolved in a carrier liquid such as chlorinated diphenyl. A pressure image such as is produced by the striking of a typewriter key releases, in areas where the pressure is applied, a small amount of the colorless marking ink and transfers it to the surface of the receiving sheet. A colored image develops in the areas where the marking ink is transferred to the reactant sheet. Such a reactant sheet and process for making it are described in U.S. Pat. No. 2,699,432 issued to Marra et al. In this patent, a reactive pigment such as attapulgite (attapulgus clay) or a zeolitic material is dispersed in an aqueous binder composition containing ammonium caseinate, sodium silicate, and 9 butadiene-styrene copolymer latex. The pigmented coating composition, when coated and dried on a paper base, produces a blue mark where it is contacted by a colorless marking ink containing crystal violet lactone. In general, it is necessary to apply 2 to 3 pounds or more per ream (1300 square feet) of the above dried coating to paper in order to fully develop the colorless dye.

The necessity of using such heavy coatings on paper has a detrimental effect on the strength properties and appearance and feel of the paper. This is particularly so where extremely thin papers are desired as the weight of the coating may be as much as 30 percent of the total paper weight. Thin papers of high strengths are necessary in the production of manifold forms where the paper is subjected to punching, perforating, folding and collating operations.

Incorporation of a reactive pigment into the paper at the wet end of the papermachine has also been tried but has not been commercially successful since large amounts of pigment, at least 16 percent of the finished paper weight, were required to produce a satisfactory colored mark with a colorless marking ink. The presence of the reactive pigment in the paper had a detrimental effect on the strength and aging properties of the paper. Furthermore, the bulk of the reactant pigment was not on the surface of the paper and, thus, sharp and clear images were not produced.

SUMMARY AND OBJECTS

It has been found that a relatively uniform thin coating of a solid phenolic reactant can be applied to a paper base by contacting said paper base with a thin film of a solution consisting essentially of said phenolic reactant in a volatile organic solvent and immediately evaporating said solvent and unexpectedly that said phenolic reactant is retained essentially completely on the contacted surface of the paper base. Thusly applied, the phenolic reactant is readily available for reaction with a colorless dye and it has been found that well defined colored marks are formed on the surface of the paper base on marking the surface with a colorless marking ink containing a colorless dye dissolved in a carrier liquid.

The amount of phenolic reactant coating necessary to produce a satisfactory mark is in the range of 0.01 to 0.2 pounds per ream of 1300 square feet (0.023 to 0.46 pound per ream of 3,000 square feet), depending somewhat on the particular phenolic reactant used. Such a small amount of coating does not materially affect the properties, particularly the strength, handling and printing properties, of the paper base to which it is applied. Thus, reactant sheets resembling light weight bond papers may be produced, whereas it was necessary to coat the prior art reactant sheets with 2 to 3 pounds per ream of reactant coating to obtain commercially acceptable paper. Such coated prior art reactant sheets do not have the handling and printing properties of bond papers and the strength properties for the same weight of paper are considerably less.

Accordingly, it is an object of this invention to provide a reactant sheeet for developing colorless dye images having improved strength, handling and printing properties.

Another object of the invention is to provide a reactant sheet in which a phenolic reactant is essentially completely retained on the paper surface and is readily available for developing colorless dye images applied thereon.

It is another object of the invention to provide a method of making the above reactant sheet.

A further object of the invention is to provide a method of producing a colored image on the surface of a reactant sheet having improved strength, handling and printing properties over those of prior art reactant sheets.

DESCRIPTION

The color developing reactants used in the present invention are essentially solid, non-volatile, water insoluble phenolic materials. Such materials must be capable of reacting with a colorless dye dissolved in a carrier liquid to produce a colored material. Since the color is developed only on intimate molecular contact of the phenolic materials with the colorless dye, the phenolic materials must be soluble at least in limited amounts in the carrier liquid. They also should be chemically stable and particularly non-reactive toward the papermaking chemicals present in the paper base. It is also desirable that the phenolic materials are relatively colorless and that they should not discolor with age. Suitable phenolic materials are characterized by having at least one position ortho to the phenolic OH group occupied by a hydrogen, halogen, hydroxyl, methyl or methylene group. A preferred group of phenolic materials are the para substituted phenol formaldehyde novolak condensation polymers, for example, a paraphenylphenol formaldehyde condensation polymer having a ring and ball softening point of 195° to 225° F.

The colorless dyes may be selected from certain of the quinoid ionic type dyes, particularly various lactone, lactam, or auramine leuco dyes such as, for example, crystal violet lactone, malachite green lactone, 1, 1-bis (para amino-phenyl) phthalen and 2, 5 dichlorophenyl leuco auramine.

The reactant coating composition is essentially a solution of the phenolic material in a volatile organic solvent. The solvent should be fast drying and should preferably dissolve up to an equal amount of the phenolic material so that the desired amounts of dried phenolic materials can be obtained by applying the thin wet films of the thickness specified by this invention. Such fast drying solvents include toluene, xylene, isopropryl alcohol, acetone, methyl ethyl ketone and butyl acetate.

The phenolic coating composition may be applied to the paper base by any method in which the paper base is brought into pressure contact with a uniform wet film of the coating composition having a thickness of substantially not more than $2 \times 10^{-4}$ inches. This corresponds to a wet film as applied to the paper having a thickness of $1 \times 10^{-4}$ inches. Above this limit, the phenolic coating composition will penetrate the paper base. For example, penetration of a 15 pound form bond paper occurred when contacted with a wet film of phenolic coating composition (50% p-phenylphenol aldehyde condensate solution in toluene) having a thickness of $2.8 \times 10^{-4}$ inches.

Below an applied thickness of $5 \times 10^{-6}$, it is impossible to obtain a uniform coating of dried phenolic material of sufficient quantity to develop a well defined colored mark. A preferred range of applied wet film thickness is $2 \times 10^{-5}$ to $8 \times 10^{-5}$ inches.

The preferred method of applying the thin coating of phenolic material is by a modified offset gravure printing means. The phenolic coating composition is metered onto an etched or engraved gravure roll by passing through a pressure nip formed by the gravure roll and a hard surfaced roll, i.e. hard rubber roll. Metered film is then transferred in part by rolling pressure contact to a roll of softer composition; i.e. a soft rubber roll, from which it is transferred to the surface of the paper base by rolling pressure contact therewith. The pressure between the soft rubber roll and a roll backing the paper is not critical but is of a low order, being just sufficient to establish positive uniform contact of the film of coating with the surface of the paper base.

Using the thin wet films of this invention and fast drying solvents, the solvent portion of the coating composition, whether by air drying or oven drying, is evaporated so quickly that penetration of phenolic material into the base is essentially eliminated. Thin coatings of phenolic materials have been applied to as widely diversified paper surfaces as porous filter paper and a dense pigment coated printing paper. Examination of the above coated papers showed that in both case phenolic material was tightly adhered to and essentially completely retained on the exposed surfaces of the top layer of fibers or pigment particles. Both of the above phenolic coated papers gave well defined colored images when tested with a colorless marking ink containing crystal violet lactone.

The concentration of phenolic material in the coating composition does not affect penetration of the composition into a paper base when applied by the method of the present invention. Coating compositions containing from 1 to 40% of a phenolic material, a paraphenylphenol formaldehyde polymeric condensate, in toluene were applied to a form bond paper without observable penetration of phenolic material. The preferred amount of paraphenylphenol is 0.02 to 0.2 pounds per ream of 1300 square feet (0.046 to 0.46 pound per ream of 3,000 square feet). Both above and below this amount, the intensity of the colored mark is poorer than within the preferred range.

At the wet film thicknesses used in the process of the present invention, viscosity of the phenolic coating composition does not affect the penetration of phenolic material. However, it has been found that using the preferred method of the present invention, it is preferred to keep viscosity of the phenolic coating composition low, in fact below that which causes an excess of liquid composition over that which is in the recesses of the gravure roll to pass between the hard rubber roll and the gravure roll.

By way of illustration, but not by way of limiting the scope of the invention, the following examples are set forth.

EXAMPLE 1

A 15 pound per ream uncoated form bond paper containing about 6% clay filler was coated at 800 feet per minute using offset gravure printing means as previously described. A 17.2% solution of paraphenylphenol formaldehyde condensate in toluene was applied in a wet film thickness of about $7.3 \times 10^{-5}$ inches and dried in a forced air oven at 188° F. to give a dried coating of condensate of 0.074 pounds per ream of 1300 square feet on the surface of the paper.

EXAMPLE 2

A 13% solution of paraphenylphenol formaldehyde condensate in toluene was applied to 15 pound form bond paper in the manner of Example 1. A $7.1 \times 10^{-5}$ inch wet film thickness of the solution was applied to the paper and the dried film was 0.055 pounds per ream.

A comparison of the properties of the coated papers prepared in Examples 1 and 2 with properties of a commercially prepared attapulgus clay coated reactant sheet is given in the following table.

| Properties | Prior Art Attapulgus clay reactant sheet | Reactant Sheet prepared by Example 1 | Example 2 | Form Bond Paper |
|---|---|---|---|---|
| Basis Weight (1300 sq. ft.) | 16.4 | 15.3 | 14.9 | 15.3 |
| Burst Factor | 19.4 | 24.2 | 25.0 | 23.6 |
| Tear Factor | | | | |
| MD | 59.7 | 71.7 | 73.6 | 73.0 |
| AM | 68.8 | 84.9 | 85.7 | 86.3 |
| Gurley Stiffness | | | | |
| MD | 68.7 | 95.5 | 93.8 | 95.5 |
| AM | 33.5 | 48.6 | 43.6 | 46.9 |
| Perforation Strength[1] | | | | |
| MD | 188 | 248 | 205 | 272 |
| AM | 305 | 411 | 406 | 469 |
| Sheffield Smoothness coat side | 93 | 113 | 116 | 124 |
| Calender Intensity[2] | 50.0 | 54.6 | 57.9 | — |
| Typewriter Intensity[3] | 62.7 | 63.2 | 65.9 | — |
| Legibility of typed characters[4] | good | good | good | — |

-continued

| Properties | Prior Art Attapulgus clay reactant sheet | Reactant Sheet prepared by Example 1 | Example 2 | Form Bond Paper |
|---|---|---|---|---|

[1] The perforation strength was determined by the method described in Patent No. 3,099,153.
[2] Calender intensity is a contrast ratio whereas the lower the numerical values, the greater the intensity of color. This value is determined by placing the coated side of a reactant paper to be tested in contact with the coated side of a standardized transfer sheet, such as is described in Patent 2,711,375 granted to Robert W. Sandberg on June 21, 1955, and then passing the superimposed papers through a calender machine, the rolls of which are subjected to a known standard load. A Bausch & Lomb Opacimeter is employed to obtain at least three measurements of the percent reflectance of the printed and unprinted areas of the reactant paper 30 seconds after calendering and the results of such measurements are averaged. The calender intensity ratio in per cent is then calculated according to the formula:

$$\text{Calender intensity} = \frac{\text{average printed area reflectance}}{\text{average non-printed area reflectance}} \times 100.$$

[3] Typewriter intensity is a contrast ratio similar to calender intensity. It is determined in a similar way to calender intensity except that instead of passing the superimposed transfer and reactant paper through a calender, closely spaced "m's" are typed on the superimposed papers using a special electric typewriter with no ribbon and the opacimeter readings are made on the reactant paper 20 minutes after typing.
[4] This is a subjective test made by typing on a transfer sheet superimposed on a reactant sheet and judging the appearance of the typed reproduction.

Coating of the form bond paper with the phenolic materials has no significant effect on the strength properties of the paper.

The superior strength properties of the paper coated with paraphenylphenol formaldehyde condensate as prepared in Examples 1 and 2 over those of the prior art attapulgus clay coated sheet are apparent from a comparison of the burst, tear, stiffness and perforation strength results. The legibility of the typed characters is equivalent to that produced on the prior art reactant sheet. The calender and typewriter intensity of the reactant sheet produced by Example 1 were 54.6 and 63.2, respectively, as compared to 50.0 and 62.7 for the prior art sheet. Calendering of the reactant sheet of Example 1 to a 90 Sheffield smoothness, as compared to the prior art sheet smoothness of 93, produced a reactant sheet with calender and typewriter values intensity of 52.3 and 62.5, respectively.

The handling and printing properties of the reactant sheet prepared in Example 1, when run on an offset form press and subsequently collated, were found to be the same as for the uncoated form bond paper.

Since the examples described are for the purposes of illustration only, it is to be understood that the present invention includes all modifications and equivalents which fall within the scope of the invention as defined by the appended claims.

What is claimed is:

1. A reactant sheet for use in developing a colored image from a colorless image formed by application of a colorless dye dissolved in a carrier liquid, which comprises a pigment coated paper base substrate having an adherent layer of pigment particles on one side, coated on said side with a uniform coating consisting of an essentially solid, non-volatile, water-insoluble, fusible phenol-formaldehyde condensation polymer which is capable of reacting with colorless dyes to form a colored material, said polymer being applied to said paper in an amount of the order of 0.01 to 0.2 pounds of solids per 1300 square feet of paper base, and said polymer being substantially completely on the surface of said paper base substrate and adherent to and essentially completely retained on the exposed surfaces of said adherent layer of pigment particles on said paper base substrate.

2. A reactant sheet according to claim 1, wherein said polymer is a substituted phenol-formaldehyde novolak condensation product in which at least one group ortho to the phenolic OH groups is a hydrogen, hydroxyl, halogen, methyl or methylene group.

3. A reactant sheet according to claim 2, wherein the said condensation polymer is the novolak condensation product of paraphenylphenol and formaldehyde.

* * * * *